United States Patent
Paz et al.

(10) Patent No.: US 9,016,112 B2
(45) Date of Patent: Apr. 28, 2015

(54) METHOD FOR DETERMINING THE MOISTURE CONTENT IN AN ABSORBENT SANITARY PRODUCT AND DEVICE FOR CARRYING OUT THE METHOD

(75) Inventors: Rui Miguel Paz, Heidenheim (DE); Susanne Beckert, Ulm (DE); Ruediger Kesselmeier, Herbrechtingen (DE); Maximilian Swerev, Augsburg (DE); Enno Gause, Heidenheim (DE); Tim Krueger, Ulm (DE); Magnus Bodmer, Neu-Ulm (DE); Oliver Gassner, Ulm (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 453 days.

(21) Appl. No.: 13/508,567

(22) PCT Filed: Oct. 30, 2010

(86) PCT No.: PCT/EP2010/006639
§ 371 (c)(1),
(2), (4) Date: Aug. 17, 2012

(87) PCT Pub. No.: WO2011/057723
PCT Pub. Date: May 19, 2011

(65) Prior Publication Data
US 2012/0312086 A1 Dec. 13, 2012

(30) Foreign Application Priority Data
Nov. 12, 2009 (DE) .......... 10 2009 054 097

(51) Int. Cl.
*G01N 33/36* (2006.01)
*G01N 15/08* (2006.01)
*G01N 5/02* (2006.01)
(Continued)

(52) U.S. Cl.
CPC .......... *A61F 13/15203* (2013.01); *G01N 5/025* (2013.01); *A61F 2013/15284* (2013.01); *A61F 2013/8491* (2013.01)

(58) Field of Classification Search
CPC ............ G01N 33/367; G01N 15/0893; G01N 33/346; G01N 5/045
USPC .................................. 73/83, 73, 74, 159, 866
See application file for complete search history.

(56) References Cited

U.S. PATENT DOCUMENTS

| 1,561,285 | A | * | 11/1925 | Sesler | 73/73 |
| 2,545,281 | A | * | 3/1951 | Hunt | 73/73 |
| 3,675,654 | A | | 7/1972 | Baker | |

(Continued)

FOREIGN PATENT DOCUMENTS

| DE | 689 04 461 | 5/1993 |
| DE | 35 88 034 | 11/1995 |

(Continued)

*Primary Examiner* — David A Rogers
(74) *Attorney, Agent, or Firm* — Paul Vincent (57) ABSTRACT

A method for determining the moisture content in an absorbent sanitary product, in particular a diaper, incontinence pad or incontinence briefs, or sanitary towel, wherein liquid is first applied to the sanitary product under preferably predetermined conditions and subsequently the article is spread out in a planar fashion. A plurality of zoned measurement areas is defined over the planar extension of the spread-out sanitary article, and a measured value is taken in each measurement area or with respect to each measurement area.

19 Claims, 8 Drawing Sheets

(51) Int. Cl.
*A61F 13/15* (2006.01)
*A61F 13/84* (2006.01)

(56) References Cited

U.S. PATENT DOCUMENTS

| | | | |
|---|---|---|---|
| 3,952,584 A * | 4/1976 | Lichstein | 73/73 |
| 4,362,157 A | 12/1982 | Keeth | |
| 5,147,343 A * | 9/1992 | Kellenberger | 604/368 |
| 5,361,627 A * | 11/1994 | Levesque | 73/73 |
| 5,425,265 A * | 6/1995 | Jaisinghani | 73/38 |
| 5,752,945 A | 5/1998 | Mosley | |
| 5,788,684 A * | 8/1998 | Abuto et al. | 604/368 |
| 5,810,797 A | 9/1998 | Menard | |
| 6,085,579 A * | 7/2000 | Herrlein | 73/73 |
| 6,298,714 B1 | 10/2001 | Courtray | |
| 6,316,687 B1 | 11/2001 | Davis | |
| 6,393,901 B1 * | 5/2002 | Levesque et al. | 73/73 |
| 6,446,495 B1 * | 9/2002 | Herrlein et al. | 73/73 |
| 6,557,398 B2 * | 5/2003 | Lindmark et al. | 73/73 |
| 6,617,489 B2 * | 9/2003 | Wada et al. | 604/368 |
| 6,655,195 B2 * | 12/2003 | Grabscheid et al. | 73/73 |
| 6,662,635 B2 * | 12/2003 | Mansky | 73/61.41 |
| 6,689,934 B2 * | 2/2004 | Dodge et al. | 604/367 |
| 6,826,973 B2 * | 12/2004 | Puckett et al. | 73/866.4 |
| 6,904,820 B2 * | 6/2005 | Tate et al. | 73/866 |
| 6,931,951 B2 * | 8/2005 | Wright et al. | 73/866.4 |
| 7,037,112 B2 * | 5/2006 | Lord et al. | 434/262 |
| 7,073,373 B2 * | 7/2006 | La Fortune | 73/73 |
| 7,174,774 B2 * | 2/2007 | Pawar et al. | 73/73 |
| 7,566,222 B2 * | 7/2009 | Harkin | 434/267 |
| 7,779,685 B2 * | 8/2010 | Kallmes | 73/159 |
| 7,795,345 B2 * | 9/2010 | Smith et al. | 524/556 |
| 2002/0043100 A1 | 4/2002 | Li | |
| 2002/0062114 A1 * | 5/2002 | Murai et al. | 604/385.01 |
| 2004/0043369 A1 | 3/2004 | Pawar | |
| 2004/0095247 A1 | 5/2004 | De Haan | |
| 2005/0258199 A1 * | 11/2005 | Honer et al. | 223/66 |
| 2007/0048709 A1 * | 3/2007 | Ales et al. | 434/262 |
| 2008/0187756 A1 | 8/2008 | Riegel | |
| 2009/0270825 A1 * | 10/2009 | Wciorka et al. | 604/367 |
| 2009/0298685 A1 * | 12/2009 | Torii et al. | 502/402 |
| 2010/0036349 A1 * | 2/2010 | Hammons et al. | 604/385.01 |
| 2010/0160888 A1 * | 6/2010 | Nakagawa et al. | 604/385.14 |
| 2010/0249739 A1 * | 9/2010 | Alkhagen et al. | 604/379 |

FOREIGN PATENT DOCUMENTS

| | | |
|---|---|---|
| DE | 696 09 943 | 4/2001 |
| DE | 699 15 014 | 12/2004 |
| DE | 10 2006 053405 | 5/2008 |
| EP | 0 312 919 | 3/1993 |
| WO | WO 03/030771 | 4/2003 |

\* cited by examiner

METHOD FOR DETERMINING THE MOISTURE CONTENT IN AN ABSORBENT SANITARY PRODUCT AND DEVICE FOR CARRYING OUT THE METHOD

This application is the national stage of PCT/EP2010/006639 filed on Oct. 30, 2010 and claims Paris Convention Priority of DE 10 2009 054 097.0 filed Nov. 12, 2009.

BACKGROUND OF THE INVENTION

The invention concerns testing methods for evaluating the function of an absorbent sanitary product, in particular a diaper, incontinence pad or incontinence briefs, sanitary towel or the like, wherein the sanitary product is to be examined e.g. in view of liquid absorption, liquid distribution, rewetting behavior or residual moisture. This is achieved, in particular, by a method for determining the moisture subsequent to prior application of liquid onto the sanitary product, advantageously under predetermined conditions.

There are numerous conventional testing and measuring methods for determining and evaluating the absorption characteristic of absorbent sanitary products of the type at issue. For example, EP 0 887 055 A1 describes a standardized process for wetting a sanitary product using a dummy having the shape of a human body, wherein the diaper is provided with a moisture sensor that is observed.

This document also discloses a standardized wetting process of a sanitary product in a spread-out planar state to be performed in a laboratory. It also describes a test for determining the rewetting behavior, wherein sections of a collage film material are applied with pressure onto the previously wetted location, and the liquid or moisture absorption thereof is determined.

The testing method UNE 153601-2 of the Spanish standards organization AENOR describes a similar test. This testing method also includes applying liquid to the center of the product length of a spread-out planar sanitary product and determining rewetting into a filter paper that has been applied and pressed onto the sanitary product.

The medical service of Germany (Medizinische Dienst Deutschland) also provides a testing method in part 3 of the test specifications 1/93 MDS-HI, which also determines rewetting after introduction of liquid under load and determines rewetting using filter paper. In this method, however, samples are initially taken from several representative points of an incontinence product, to which synthetic urine is applied and which are then measured. This method is not performed in a non-destructive fashion and is therefore remote from practice.

A similar method is described in the Italian testing method NMC 93 part numbers 1 to 3 for testing the absorption capacity, absorption speed and retention power of incontinence products. In this connection, samples of a size of 100×100 mm are removed from a front, center and rear area of an incontinence product. The removed samples are wetted and then disposed onto a draining lattice and loaded in a predetermined fashion. Rewetting is subsequently determined as the difference between the dry and the we sample.

The test has little relevance for actually occurring wear situations of the intact sanitary product due to destruction of the absorbent area of the sanitary product and complete wetting of the samples.

In the conventional methods, each parameter to be measured is determined in unrealistic test situations, which substantially differ from wear situations that actually occur during use of a sanitary product. The results of the conventional test methods therefore do not give any reliable conclusions about the function of a sanitary product during actual use. This was realized with the present invention.

It is the object of the present invention to provide a method of the above-mentioned type and as described in the independent claim, which permits realistic conclusions regarding the operational behavior and, in particular, liquid absorption characteristics, liquid distribution characteristics or rewetting characteristics of a sanitary product.

SUMMARY OF THE INVENTION

In accordance with the invention, this object is achieved in a method of this type in that a plurality of zoned measurement areas are defined over the planar extension of the spread-out sanitary product and one measured value is taken for each measurement area or with respect to each measurement area.

The present invention therefore proposes to observe and measure a sanitary product after wetting, thereby optimally simulating reality, and at a plurality of locations in order to be able to gain realistic information about the operational behavior of the sanitary product. Realistic information about the operational behavior of the sanitary product can be gained in a detailed fashion for the respectively considered zoned measurement areas, i.e. located at reproducible points of the sanitary product, since the entire intact sanitary product is wetted, preferably in a configuration in which it is actually worn, and then measured at a plurality of locations, namely in the zoned measurement areas. It should be pointed out that, in accordance with the present invention, "determination of the moisture of a sanitary product" subsumes any measurement performed in connection with the liquid amount absorbed by the respective zoned measurement areas of the sanitary product.

It has turned out to be particularly advantageous for the measurement areas to include at least 50%, in particular at least 60%, in particular at least 70%, in particular at least 80%, and moreover, in particular, at least 90% of the planar extension of the absorbent area of the sanitary product, wherein the absorbent area means the layers that are used for permanent storage.

As mentioned above, the considered sanitary product is advantageously tested in a non-destructed state, advantageously including its absorbent areas and chassis components, wherein in view of the planar extension of the sanitary product any disturbing elastification means may be removed or deactivated.

The liquid may advantageously be introduced into the sanitary product by using a test dummy to which the sanitary product is applied. The liquid may be introduced in accordance with the desired wear situation to be considered, e.g. when the test dummy wearing the sanitary product has been brought into a dorsal or side position or also in an upright standing or a sitting position. This influences the liquid distribution within the sanitary product and its absorbent element, which can be quantitatively detected by the subsequent measurement of the zoned measurement areas of the sanitary product.

In a further embodiment of the invention, a template is advantageously used for defining and, if necessary, physically delimiting the zoned measurement areas. This template may e.g. have a plurality of zoned measurement areas that are arranged in transverse and longitudinal rows, have equal or different sizes and may have any geometrical shape, however, conveniently a square or round shape. The template may be designed to be rigid or preferably slightly flexible. It may e.g. have a marking which may be aligned with respect to a marking, in particular, a geometrical center of the sanitary product in relation to the chassis or advantageously in relation to the absorbent area, or may be aligned with respect to an edge or the like marking of the sanitary product and be arranged on the spread-out planar sanitary product.

The mentioned template advantageously has through-holes that are delimited from each other by webs. The height of the webs may typically be in the range of a few millimeters up to suitably 20 mm. Their width is typically a few millimeters, in particular, 1 to 8 mm.

The size of the measurement areas, such as length or width, is advantageously in one direction 10 to 100 mm, in particular 10 to 80 mm, in particular 20 to 60 mm, in particular 30 to 50 mm and in another direction 10 to 100 mm, in particular 10 to 80 mm, in particular 20 to 60 mm, in particular 30 to 50 mm.

The part of the surface of the sanitary product covered by the webs with respect to the overall surface of the measurement areas is advantageously less than 20%, in particular, less than 15% and moreover, in particular, less than 10%.

The measurement per se may be performed in each zoned measurement area in any fashion. It has turned out to be advantageous to perform the measurement through determination of the weight difference, measurement of an electrical property, in particular spectroscopic measurement of an optical property, in particular through measurement using microwaves or through measurement of the thermal conductivity. In this fashion, one can determine a respective measure of the amount of liquid absorbed in a respective measurement area of the sanitary product. The above-mentioned measurement through determination of the weight difference e.g. also includes consideration of the rewetting behavior by transferring liquid that is not permanently bound from one respective measurement area to a transfer means and determining the respective amount of the transferred liquid by any measurement per se, in particular, by measurements of the weight difference on the transfer means.

The measured value is thereby advantageously determined in that a transfer means for liquid is applied to a respective measurement area and the transfer means and the respective measurement area are loaded with pressure such that liquid can pass from the measurement area into the transfer means and the measurement value is then taken from the transfer means. The mentioned transfer means may advantageously be filter paper.

In accordance with a further embodiment of the invention, it would be feasible and advantageous to use a flatly extending plate-shaped and liquid-absorbing porous transfer means, which is applied to or disposed on at least part of the planar extension of the spread-out sanitary product, wherein in this case, the transfer means itself advantageously has zones. In this connection, liquid stored in the sanitary product is transferred to the flatly extending plate-shaped porous transfer means. By means of the transfer means, a mirror image or imprint of the liquid distribution in the sanitary product is virtually obtained and is transferred to the transfer means. Areas or zoned measurement areas of the sanitary product are thereby imaged on the planarly extending porous transfer means. Areas in which more (not permanently bound) liquid is absorbed, discharge a correspondingly larger amount of liquid to the transfer means than areas with a smaller amount of not permanently bound liquid. Whenever a transfer means is used, the measured values taken from the transfer means also provide information about the rewetting behavior of the sanitary product.

It is basically feasible to design the flatly extending plate-shaped and liquid-absorbing porous transfer means in a homogeneous fashion over its planar extension, i.e. a priori without zones. In this case, it would be advantageous to perform measurements substantially directly after the mirror-like transfer of the liquid distribution in the sanitary product to the transfer means, i.e. without substantial delay, such that information can be gained about the liquid distribution in the sanitary product, i.e. with respect to the zoned measurement areas that are at least virtually applied to the sanitary product without the occurrence of further changes due to liquid flow in the transfer means.

In a further development of the flatly extending plate-shaped porous transfer means, the transfer means itself is advantageously designed in zones in that it comprises separating webs without porosity, which prevent liquid absorption and/or liquid flow, or cuts in a Z direction, which prevent liquid absorption and/or liquid flow. When the three-dimensional porous structure of the plate-shaped transfer means has non-porous separating webs, three-dimensional measurement areas are formed, which are separated from each other and between which liquid cannot flow. It is thereby advantageously prevented that the mirror-like image of the liquid storage transferred from the sanitary product to the transfer means changes again due to capillary effects within the transfer means. The same may be realized through cuts or separating slits extending in the Z direction in the transfer means.

In particular, when information is given about the rewetting behavior of sanitary products, it has turned out to be advantageous when the flatly extending plate-shaped and liquid-absorbing porous transfer means and the spread-out planar sanitary product are pressed against each other prior to and/or during measurement. A wear situation can be simulated in this fashion. Pressing plate-shaped transfer means and sanitary product against each other can be realized in that the transfer means is pressed onto the spread-out planar sanitary product with a predetermined pressure. The sanitary product may thereby also be supported on a three-dimensionally structured support in order to provide a pressure that varies over the planar extension. The pressure could alternatively also be exerted from the side of the sanitary product opposite to the transfer means.

Irrespective of the use of one or more transfer means, it is advantageous to pressurize all measurement areas or part of the measurement areas prior to performing a measurement, wherein the pressure for all or part of the measurement areas is individually predetermined in correspondence with a wear situation of the sanitary product to be simulated. Application of pressure to the sanitary product prior to measurement can therefore be used to create a situation that is as close to reality as possible and again influences the liquid distribution within the sanitary product. As a result, the measured values provide realistic information about the function of the sanitary product.

Measurement areas located in the edge area of the absorbent area of the sanitary product are advantageously not taken into consideration in the measurements when the measurement area covers less than approximately 33% of the absorbent area. The surface portion of the edge areas that are not measured may be between approximately 0.5 and approximately 8.0% of the overall absorbent area in dependence on the contour and the product size.

In the light of the foregoing, one substantial idea of the present invention consists in that a plurality of zoned measurement areas, which advantageously include a considerable part, in particular, at least 50% of the planar extension of the absorbent area of the sanitary product, are considered at the same time and are, in the broadest sense, simultaneously or substantially simultaneously measured to determine the moisture. The term of simultaneity thereby means that the overall sanitary product comprising the measurement areas is loaded with liquid, wherein the liquid is distributed in the sanitary product in correspondence with its liquid absorbing characteristics and is stored on a more or less permanent basis in dependence on the composition of the absorbent components of the sanitary product (e.g. pulp or super absorbent materials). After a predetermined time, a plurality of zoned measurement areas of the sanitary product are simultaneously observed and measured although the actual measurement is not performed exactly at the same time for all measurement areas, rather successively. This would e.g. be the case when a spectroscopic sensor scans one measurement area after the other during a measurement or when the weight difference of transfer means that have been previously simultaneously been pressed onto the sanitary product is determined successively.

The present invention also concerns a device for performing the inventive method, wherein the device comprises a device for determining the moisture in a respective measurement area to be considered or with respect to a respective measurement area to be considered. This may e.g. be a device in which the measurement is performed directly in the zoned measurement areas in that the device is moved to a measuring position of the sanitary product that is flatly spread-out on the device and the zoned measurement areas are then measured either successively or at the same time. The zoned measurement areas could e.g. be determined successively, but nevertheless substantially simultaneously in the course of a scanning measurement.

In a further embodiment of the invention, the device for performing the method is characterized by a configuration of means for applying pressure onto the measurement areas, which corresponds to the configuration of the zoned measurement areas. In this fashion, an operating pressure on the sanitary product can either be simulated, as it typically occurs in different wear situations, or the configuration of pressure-exerting means is used for wetting transfer means in the form of filter papers or the like in order to detect rewetting of the sanitary product through unbound liquid in the zoned measurement areas.

In the simplest case, the means for applying pressure may be designed by a zoned or unzoned plate that at least partially extends over the sanitary product and is applied, in particular pressed, onto the spread-out planar sanitary product. The plate may advantageously be transparent or at least be permeable to microwaves. In this fashion, it would even be possible to perform a measurement of the measuring areas of the sanitary product while a pressure is being exerted, in particular, when optical and, in particular, spectroscopic measurement methods are used, in particular, using microwaves or infrared. It is then also possible to vary the applied pressure and then obtain liquid storage profiles quasi in dependence on the pressure based on the measurement performed in the zoned measurement areas or with respect to the zoned measurement areas. As mentioned above, it is also feasible to dispose the sanitary product onto a predetermined three-dimensionally structured surface in order to simulate different pressures, or it would be feasible to exert a pressure onto the sanitary product from the opposite side of the plate, wherein the pressure varies, in particular, over the planar extension, and to provide corresponding means for this purpose.

It has moreover turned out to be advantageous for the device to comprise a template that can be disposed onto the spread-out planar sanitary product to define the measurement areas. In this case, it is also advantageous for the configuration of means for applying a pressure onto the measurement areas to extend through the template. In this case, the template is advantageously applied onto the side of the spread-out planar sanitary product facing the body. When transfer means are used, they can be inserted into the openings of the template that define the measurement areas, and the means for applying a pressure onto the measurement areas subsequently extend through the template and load the transfer means and the sanitary product.

In accordance with a further inventive idea, the means for applying a pressure onto the measurement areas are advantageously designed in such a fashion that an individually predeterminable pressure can be applied on each measurement area. This simulates per se any wear or load situation of the sanitary product such that, during establishment of equilibrium with respect to liquid absorption, liquid distribution and liquid storage in the absorbent components of the sanitary product, measurements in the zoned measurement areas are then based on this establishing state of equilibrium.

It has also turned out to be advantageous for the device to comprise a base that forms a planar support for applying the sanitary product, and a mechanical device for moving the configuration of means for exerting pressure onto the measurement areas into a work position with respect to the planar support. The mechanical device may be designed like a portal such that a cross member of the portal on which the means for exerting a pressure are arranged extends above the planar support and therefore of the sanitary product. A configuration of means for applying pressure onto the sanitary product could alternatively also be integrated in the support for the sanitary product such that only one planar counter pressure means from above is required.

The configuration of pressure-exerting means may comprise a plurality of dies, which can advantageously be individually controlled and/or moved independently of each other and be applied against the measurement areas.

In particular, for evaluating the rewetting behavior, it has turned out to be advantageous to provide a flatly extending plate-shaped and liquid-absorbing porous transfer means which can be applied at least over part of the planar extension of the spread-out sanitary product, and to form the means for determining the moisture for performing measurements on the flatly extending plate-shaped transfer means. In this case, a mirror image of the liquid storage in the sanitary product can be transferred onto the flatly extending porous transfer means as described above, wherein in this case, the measurement is performed on the transfer means, which nevertheless allows a statement about the amount of liquid in a certain area of the sanitary product, i.e. in a zoned measurement area of the sanitary product. Also in this case, it has turned out to be advantageous to provide a device for pressing the spread-out planar sanitary product and the flatly extending plate-shaped and liquid-absorbing porous transfer means that has been applied to the sanitary product, against each other. This device may comprise means for applying pressure, which load the sanitary product from the side opposite to the transfer means.

Further features, details and advantages of the invention can be extracted from the attached claims, from the drawing and the description of the inventive method. In the drawing:

DESCRIPTION OF THE PREFERRED EMBODIMENT

Figure 1:
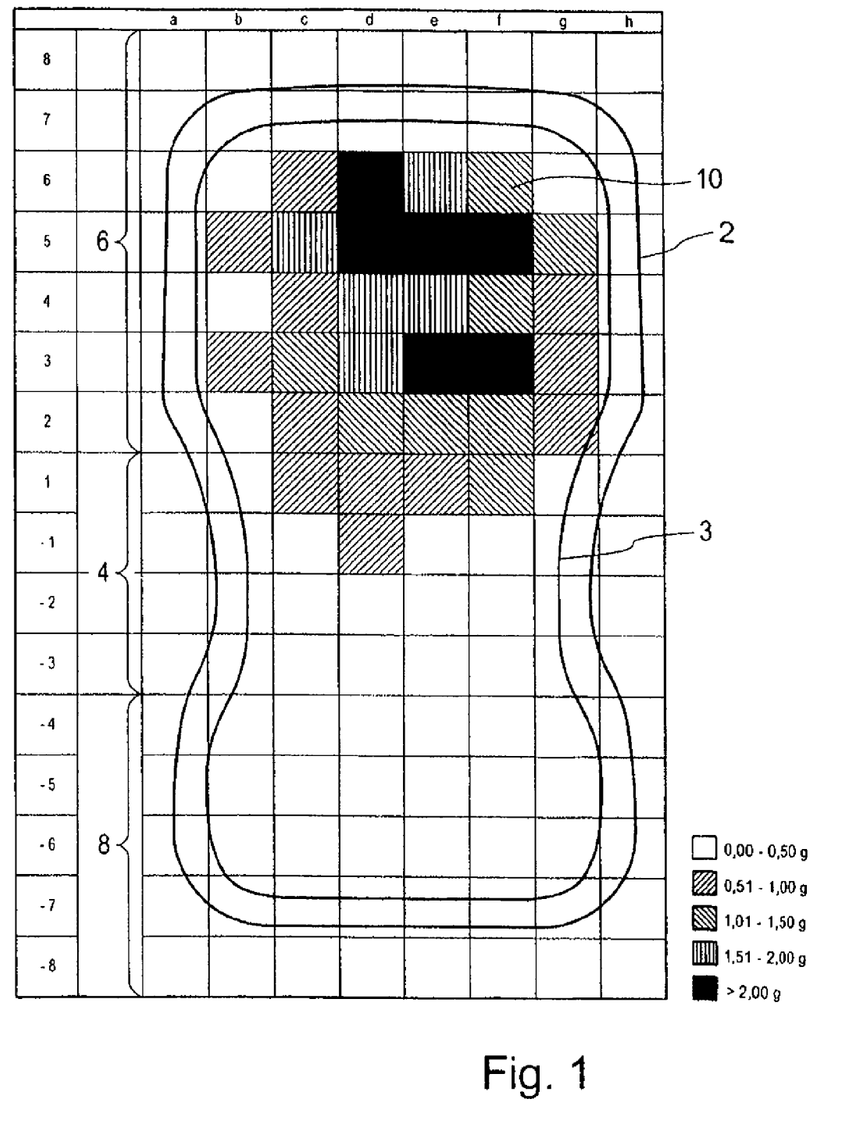
FIG. 1 shows a schematic top view of an absorbing sanitary product with indicated zoned measurement areas.

FIG. 1 shows a schematic top view of an absorbent sanitary product in the form of an incontinence pad 2 having a width of approximately 300 mm and a length of approximately 600 mm. The incontinence pad 2 comprises an absorbent area 3. The crotch area 4, indicated by a smaller width, comes to rest between the legs of the user. The rear area 6 extends to the rear past the bottom of the user and the front area 8 extends towards the belly side of the user. The incontinence pad 2 may e.g. be retained on the body of the user by mesh briefs. The invention naturally also includes sanitary products, which can be closed on themselves by closure elements and can therefore be worn on the body of the user.

FIG. 1 also indicates a plurality of zoned measurement areas 10 which, by way of example, have a square dimension with a side length of approximately 40 mm.

Figure 2A:
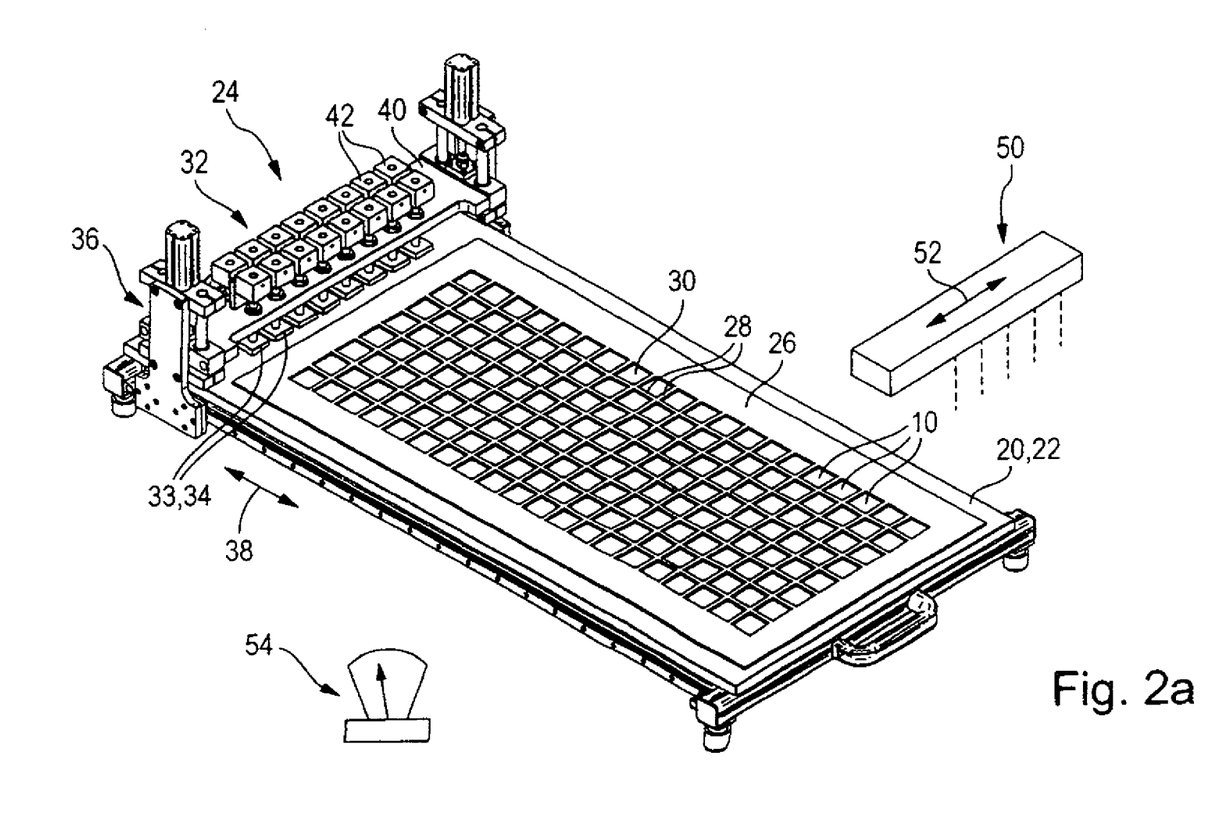
FIGS. 2a-e show different views of a measurement device.
Figure 2B:
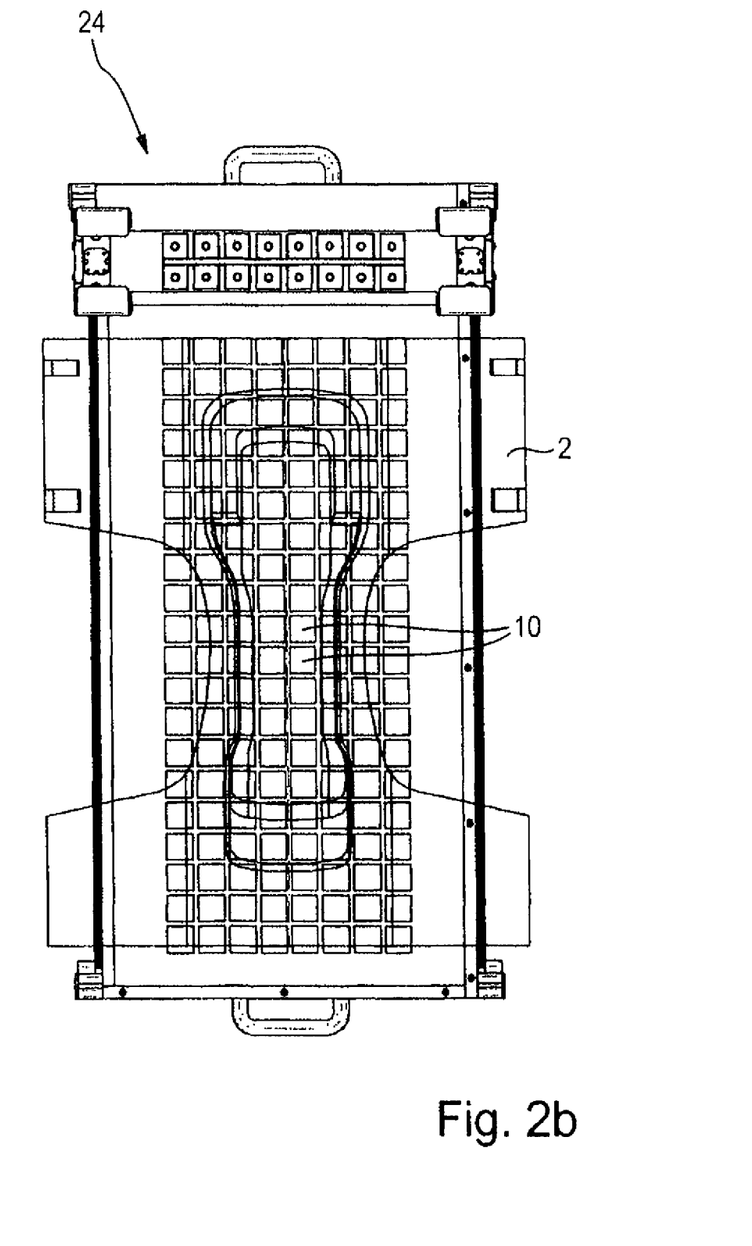

In accordance with the invention, a measured value is determined for each measurement area 10 or a plurality of measurement areas 10 in an area of interest of the sanitary product, wherein the value relates to the amount of liquid stored in the respective measurement area. For this purpose, the sanitary product is loaded with a certain amount of liquid in an advantageously standardized method. This may be performed by way of example in the spread-out planar state of the sanitary product as indicated in FIG. 1, or the sanitary product is applied to a user as intended and loaded with liquid, or it is applied to a test device in the form of a dummy having the shape of a human body, and loaded with liquid in the applied state, if necessary, additionally simulating loads that occur during standing, lying down or sitting. In this connection, several, in particular four micturitions, of a certain amount of liquid, e.g. 200 ml each, are introduced into the sanitary product in a predetermined time interval of, in particular, 5 minutes. After a further time interval of e.g. 5 minutes, the sanitary product is removed from the user or the test device (dummy) and flatly spread out, e.g. on a base 22, forming a planar support 20, of a measuring device designated in total by reference numeral 24 and illustrated in FIG. 2. In order to define a plurality of zoned measurement areas 10, a template 26 is applied onto the spread-out planar sanitary product, which is not shown in FIG. 2. The template comprises a plurality of through-holes 30 which are delimited by webs 28 and delimit or define the plurality of measurement areas 10. It is explicitly pointed out that it is not absolutely necessary to use a template for defining the plurality of zoned measurement areas 10.

Figure 3:
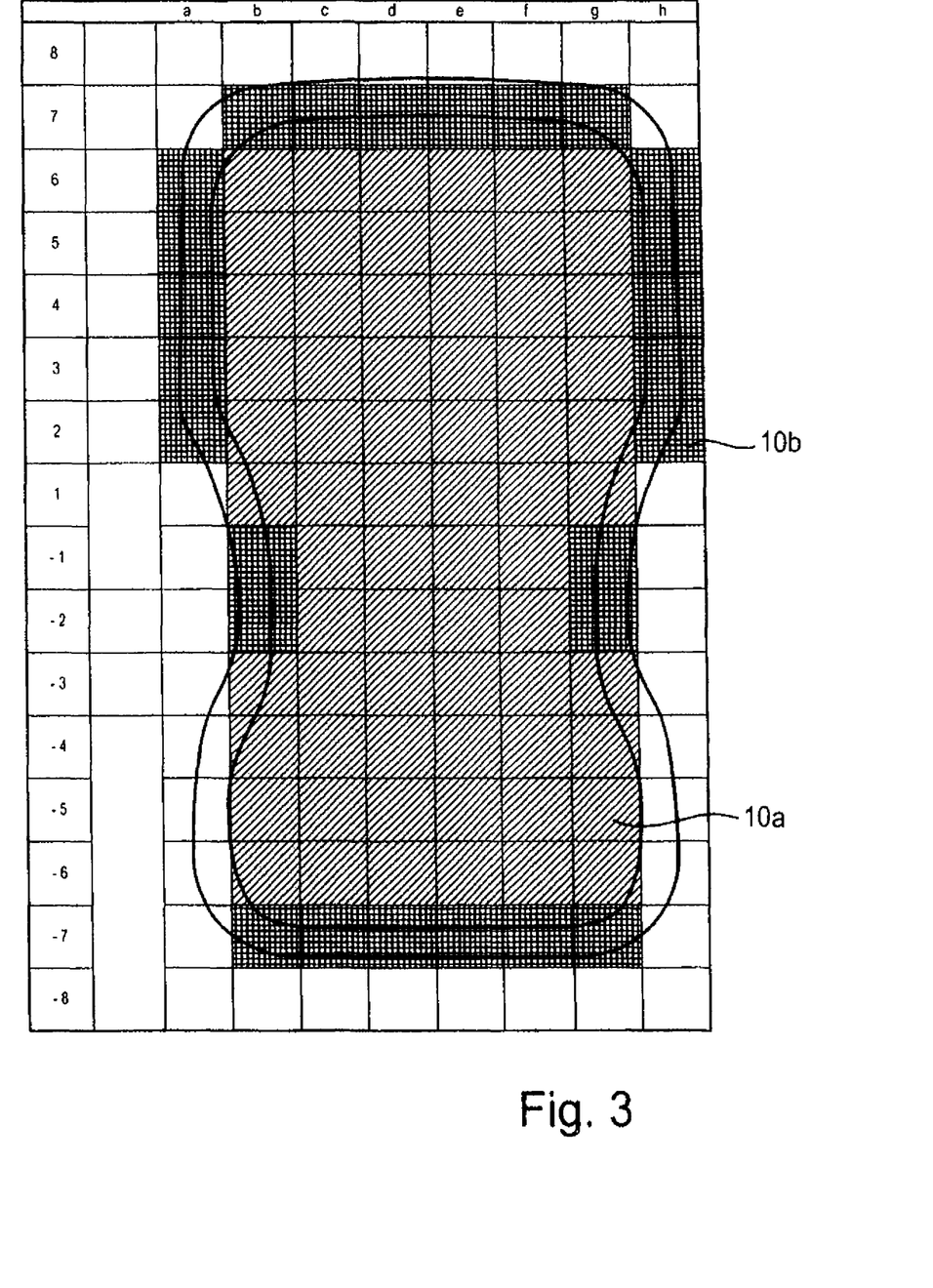
FIG. 3 shows a schematic top view of an absorbing sanitary product with measured measurement areas and non-measured measurement areas in the border area.

A measured value can be taken through these openings 30 for each measurement area 10, which value relates to the moisture or the liquid absorbed by the sanitary product. FIG. 3 shows the measurement areas 10a, for which a measurement is performed, and also the measurement areas in the border area 10b, which cover less than approximately 33% of the absorbent area and for which advantageously no value is measured or taken into consideration in the evaluation.

The liquid amount that can be extracted from the sanitary product, i.e. the rewetting liquid amount may e.g. be determined as a measure for the rewetting behavior of the sanitary product. For this purpose, a configuration of transfer means 31, e.g. in the form of a 10-layered pile of filter paper (type no 3 Whatman) may be introduced into a respective measurement area 10, which is then pressed against the upper side of the wetted sanitary product facing the body, by exerting a pressure onto the respective measurement areas, wherein the filter papers can absorb only loosely stored liquid. This is then measured by determining the weight difference between the dry and wetted filter paper pile (specified in grams, measuring accuracy 0.01 g). The template 26 supports or delimits and retains the configuration of transfer means 31 in the form of filter papers in the respective measurement area 10.

Figure 2C:
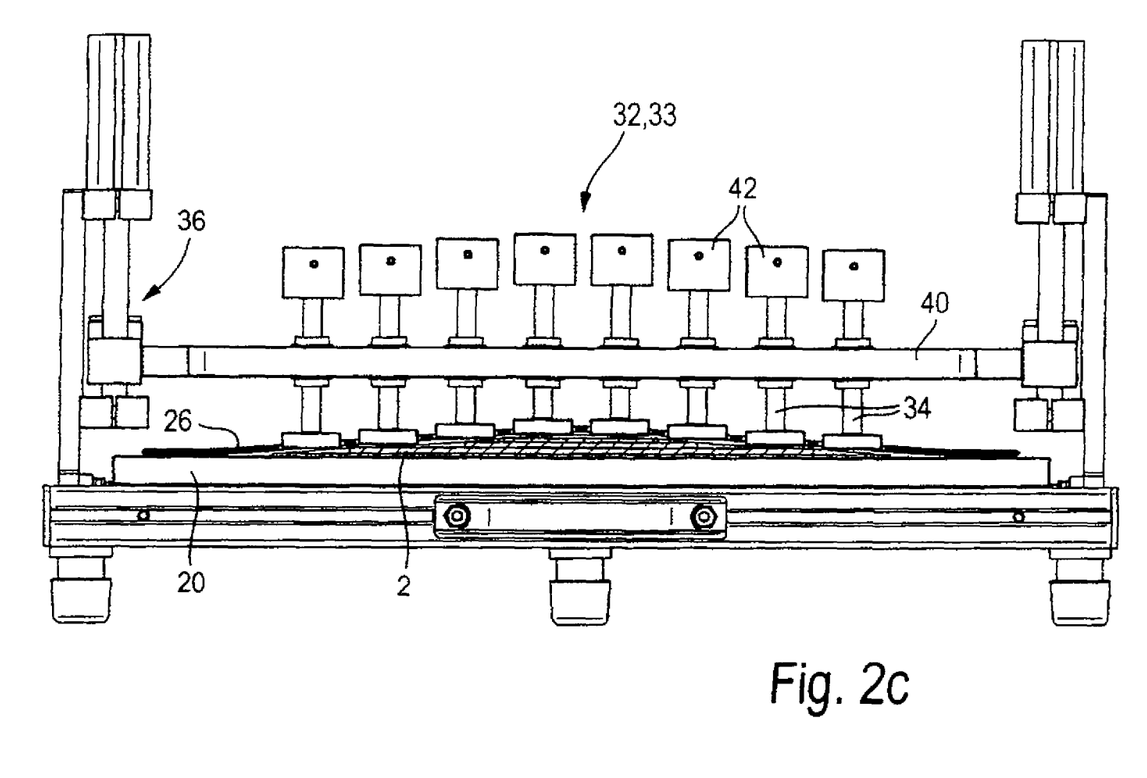
Figure 2D:
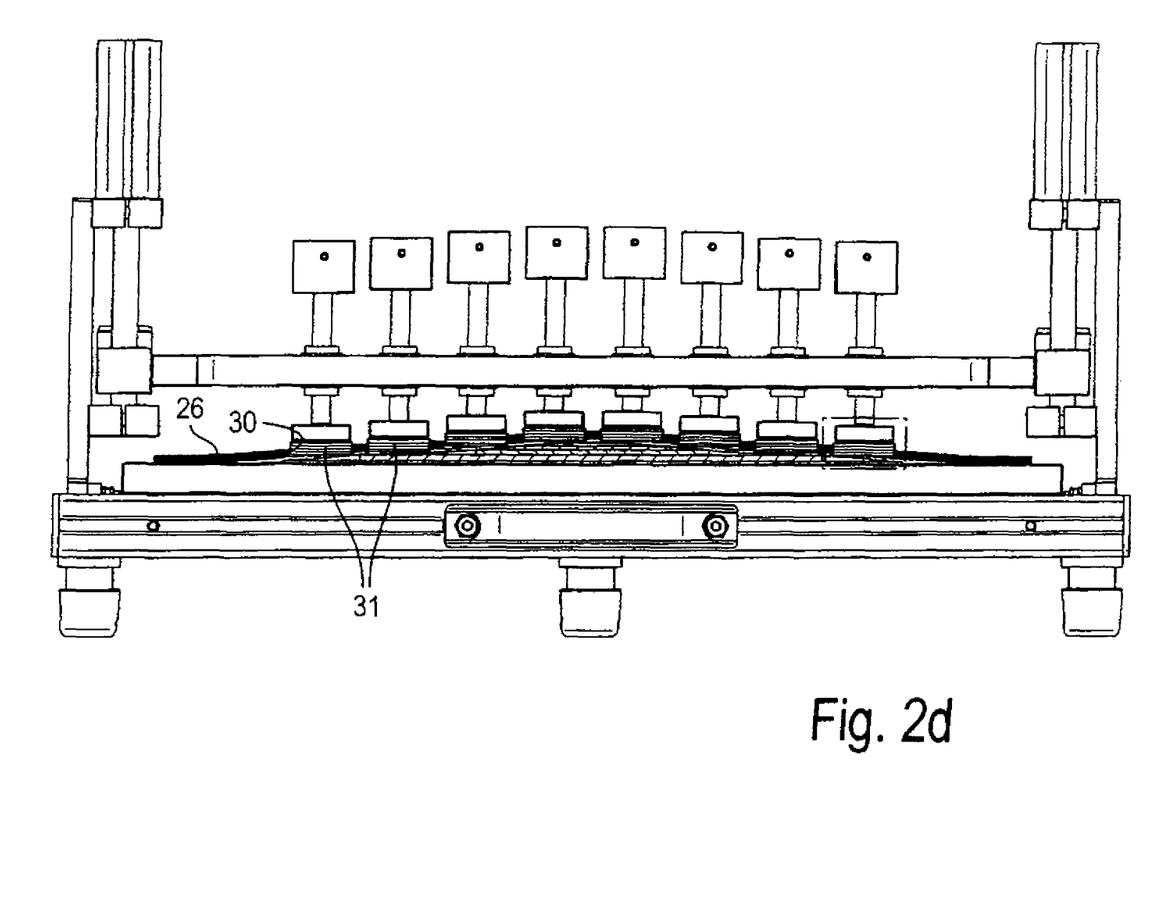
Figure 2E:
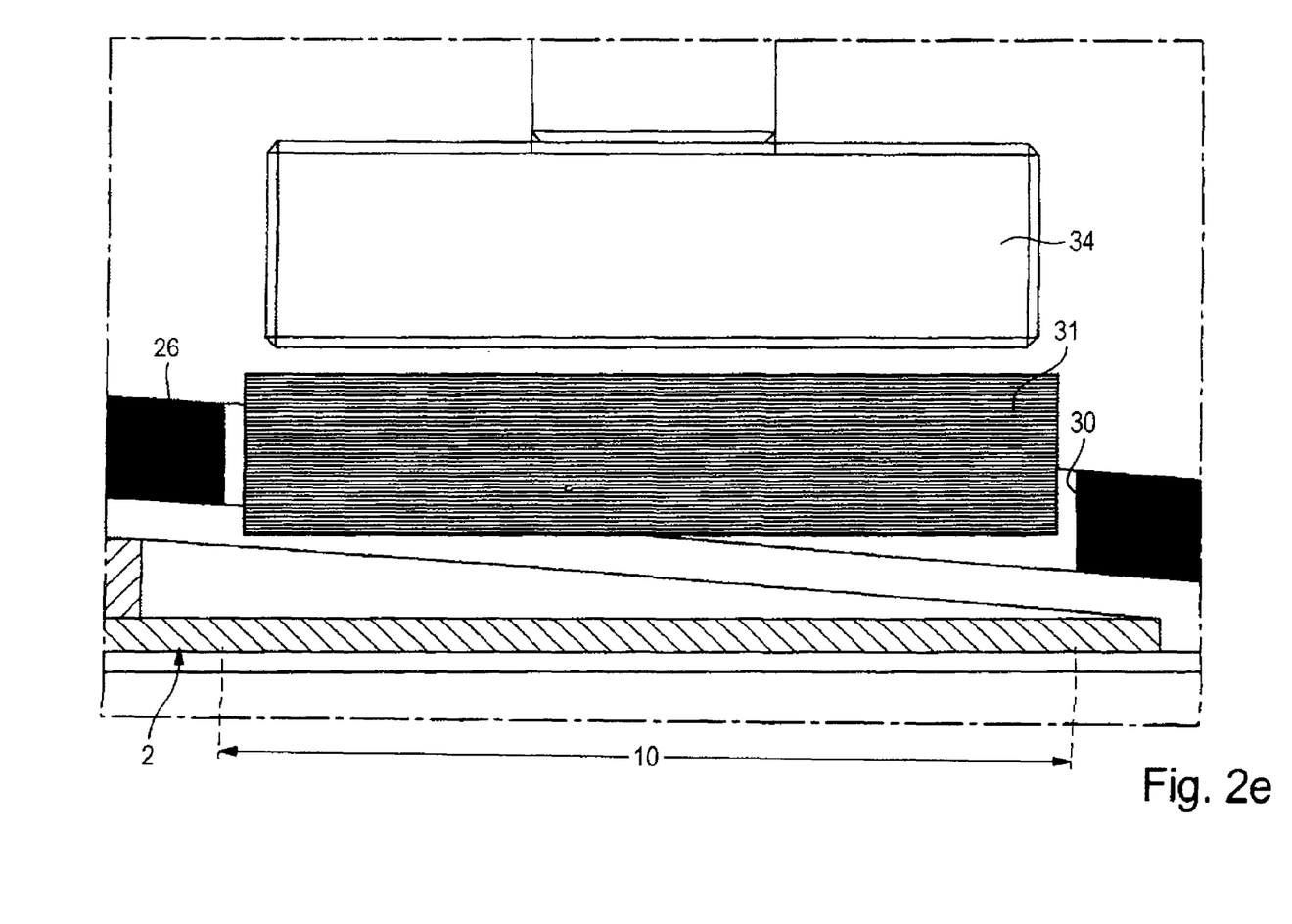

The device 24 comprises an array-like configuration of e.g. 8×2 pressure-generating means 33 in the form of dies 34 which can be lowered perpendicularly to the plane of the planar support 20 through the openings 30 of the template 26 onto the sanitary product. The dies 34 can be lowered independently of each other. One can see from FIGS. 2c and 2d, that the dies 34 that can be lowered independently of each other can be adjusted to the topology of the absorbent element, which greatly locally varies in dependence on the liquid load. Super absorbent polymer materials can store considerable amounts of liquid in that they change into a gelled state and thereby considerably swell. FIG. 2c shows a cross-section through the measuring device according to FIGS. 2a, b without transfer means 31 and FIG. 2d with transfer means. The template 26 which is advantageously but not necessarily provided is used in both cases. FIG. 2e clearly shows in an enlarged sectional view the retaining or centering effect of the template 26 on the positioning of the transfer means 31 in the respective measurement areas 10, in particular, in the area of a stepped absorbent element topology.

The configuration 32 of pressure-generating means is held by a mechanical device 36 such that it can be displaced in a longitudinal direction in the direction of the double arrow 38 and can thereby be brought into a work position with respect to the zoned measurement areas 10 of the sanitary product. The mechanical device 36 is designed like a portal and the configuration 32 with the dies 34 is arranged on a cross member 40 extending in a horizontal direction over the planar support 20. The pressure exerted by the dies 34 through the openings 30 of the template 26 onto the sanitary product results in the present exemplary case from the weight of the weights 42 applied to the dies 34, in the present case 35 g/cm$^2$. It is clear, that further technical designs are feasible, e.g. that the individual means 33 or dies 34 can be force-loaded pneumatically or hydraulically or in any other fashion and/or that an individual pressure can be adjusted for every individual pressurization means 33 or die 34. This offers the possibility to use the pressurization means 33 not only for moistening the transfer means but also for simulating different load situations of the wetted sanitary product prior to measurement. In the measuring device 24 shown by way of example in FIG. 2a, two respective lines of the zoned measurement areas 10 are simultaneously loaded using the array-like configuration 32 of the pressurization means 33. Two further lines of zoned measurement areas and any transfer means provided therein (FIGS. 2d, e) are subsequently loaded. It is clear that it is also possible to simultaneously load all measurement areas or all measurement areas to be taken into consideration in the course of the measurement.

The transfer means 31 wetted in this fashion are then individually weighed as mentioned above and the absorbed amount of liquid is determined and then allocated to the individual zoned measurement areas 10, which is illustrated by way of example in FIG. 1 through entries in the measurement areas 10. The rewetting behavior or a different parameter associated with the absorption of liquid may then be determined for a plurality of zoned measurement areas. The measurement of all measurement areas to be considered is performed at a room temperature of 21 to 23° C. within maximally 30 minutes in order to minimize influences due to evaporation.

FIG. 2a further schematically shows a device 50 for determining the moisture of a respective measurement area 10 to be measured which, by way of example, can be moved in the direction of the double arrow 52 and be brought into a work position above the planar support 20 and the measurement areas 10. This may e.g. be a spectroscopic measuring device which can measure the measurement areas 10 and for this purpose can be moved in the direction of the double arrow 38 in a substantially scanning fashion over the measurement areas 10. If liquid-absorbing transfer means are used, as described above, a means 54, which is schematically indicated, for determining the moisture may comprise a weighting function for the transfer means.

Figure 4A:
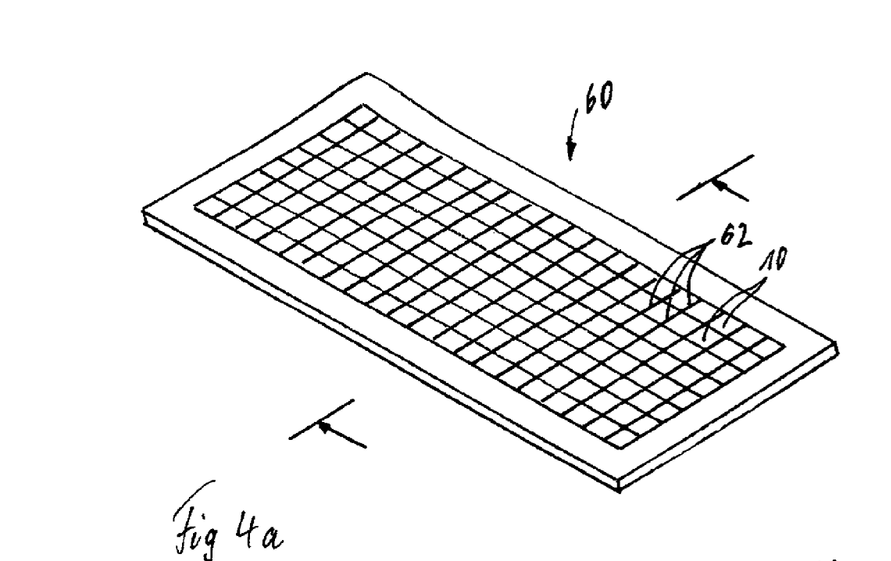
FIG. 4a shows a perspective view of a plate-shaped porous transfer means.

FIG. 4a shows a perspective view of a flatly extending plate-shaped and liquid-absorbing porous transfer means 60. This transfer means 60 is preferably zoned in that it has a plurality of non-porous webs 62 which quasi subdivide the three-dimensional porous structure into measurement areas 10 which are separated from each other to prevent transport of liquid between them within the transfer means 60. Separating slits may alternatively also be provided instead of these webs 62 that extend in a cross-shape, wherein in this case, the separating slits do not extend over the entire depth of the three-dimensional porous structure, or a further plate-shaped holder for the measurement areas may be provided, in particular, in the form of a Plexiglas plate.

Figure 4B:
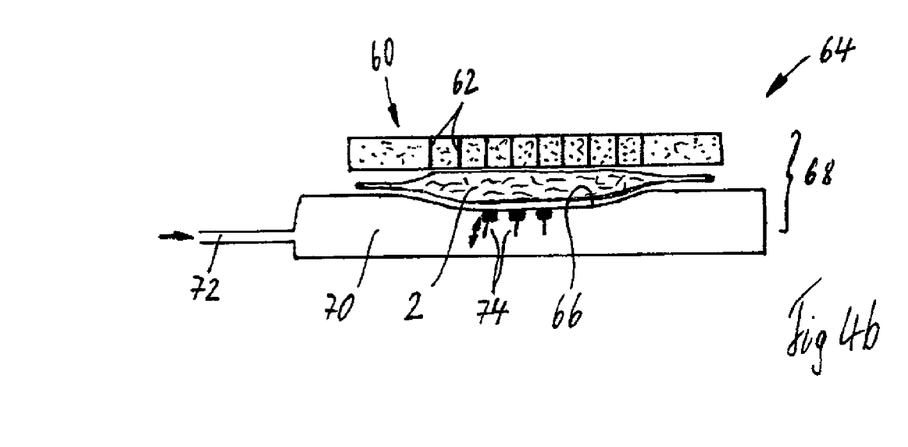
FIG. 4b shows a sectional view through the transfer means in a measurement configuration.

FIG. 4b schematically shows an exemplary measuring configuration 64, in which an incontinence pad 2 is flatly spread out on a three-dimensional support 66. The plate-shaped porous transfer means 60, shown in FIG. 4a, is e.g. disposed on top of it, wherein FIG. 4a indicates the sectional plane. In this case, the plate-shaped porous transfer means 60 and the support 66 form a means 68 for pressing the incontinence pad 2 and the transfer means 60 against each other. When the transfer means 60 is uniformly pressed against the support 66, a pressure profile is obtained that can be predetermined in accordance with the shape of the support 66 and in accordance with the material distribution within the incontinence pad 2. FIG. 4b moreover indicates that the element 70 forming the support 66 may e.g. be designed to be expandable by introducing a pressurized medium e.g. via a connection 72. Pressure-exerting means 74 that can be adjusted in the Z direction may alternatively be provided in the element 70 forming the support 66, as is also indicated in FIG. 4b. After mirror image-like transfer of the liquid distribution within the incontinence pad 2 to the transfer means 60, measurement is performed on the transfer means 60 according to one of the above-described measurement methods in order to obtain quantitative information about the liquid distribution in the considered measurement areas. When the transfer means 60 is suitably designed, it would even be feasible to perform measurement directly with the measurement configuration 64 illustrated in FIG. 4b by using a suitable measuring instrument in that the measuring device accesses the upper side of the transfer means for measurement.

We claim:

1. A method for determining a moisture content of an absorbent sanitary product, a diaper, an incontinence pad, incontinence briefs or a sanitary towel, the method comprising the steps of:
   a) applying liquid to the sanitary product under predetermined conditions;
   b) spreading out, following step a), the sanitary product in a flat manner;
   c) defining a plurality of zoned measurement areas over a planar extension of a spread-out sanitary product; and
   d) taking one measured value for each measurement area or with respect to each measurement area, wherein respective measured values are taken in that a plurality of transfer elements for liquid are simultaneously applied to the plurality of respective zoned measurement areas and respective transfer elements are simultaneously pressed onto the respective zoned measurement areas such that liquid passes from the respective measurement areas into the respective transfer elements, wherein a measurement is subsequently performed on the respective transfer elements.

2. The method of claim 1, wherein the measurement areas include at least 50%, at least 60%, at least 70%, at least 80% or at least 90% of a planar extension of an absorbent area of the sanitary product.

3. The method of claim 1, wherein a template is used for defining and or physically delimiting the measurement areas.

4. The method of claim 3, wherein the template has through-holes which are delimited from each other by webs.

5. The method of claim 1, wherein the measurement areas have a size in a first direction of 10 to 100 mm, 10 to 80 mm, 20 to 60 mm or 30 to 50 mm and in a second direction of 10 to 100 mm, 10 to 80 mm, 20 to 60 mm or 30 to 50 mm.

6. The method of claim 1, wherein a measurement is performed by determining a weight difference, by measurement of an electrical property, by spectroscopic measurement of an optical property, by measurement using microwaves or by measurement of a heat conductivity.

7. The method of claim 1, wherein a flatly extending plate-shaped and liquid-absorbing ,porous transfer element is applied to at least part of a planar extension of the spread-out sanitary product, wherein the transfer element has zones.

8. The method of claim 7, wherein the flatly extending plate-shaped and liquid-absorbing porous transfer element zones are defined by non-porous, separating webs, which prevent liquid absorption and/or liquid flow or by cuts in a Z direction, which prevent liquid absorption and/or liquid flow.

9. The method of claim 7, wherein the flatly extending plate-shaped and liquid-absorbing porous transfer element and the spread-out planar sanitary product are pressed against each other prior to and/or during a measurement.

10. A method for determining a moisture content of an absorbent sanitary product, a diaper, an incontinence pad incontinence briefs or a sanitary towel, the method comprising the steps of:
   a) applying liquid to the sanitary product under predetermined conditions:
   b) spreading out, following step a), the sanitary product in a flat manner;
   c) defining a plurality of zoned measurement areas over a planar extension of a spread-out sanitary product: and d) taking one measured value for each measurement area or with respect to each measurement area, wherein all or part of the measurement areas of the sanitary product are pressurized prior to measurement, a pressure being predetermined for all or part of the measurement areas in correspondence with a situation to be simulated.

11. A device for performing a method, the method for determining a moisture content of an absorbent sanitary product, a diaper, an incontinence pad, incontinence briefs or a sanitary towel, the method comprising the steps of:
   a) applying liquid to the sanitary product under predetermined conditions;
   b) spreading out, following step a), the sanitary product in a flat manner;

c) defining a plurality of zoned measurement areas over a planar extension of a spread-out sanitary product; and
d) taking one measured value for each measurement area or with respect to each measurement area;

the device comprising:
an element for determining the moisture in a respective measurement area to be considered or with respect to a respective measurement area to be considered, wherein said element for determining the moisture comprises a configuration for applying pressure onto the measurement areas in correspondence with a configuration of zoned measurement areas;
a planar support forming a base for supporting the sanitary product; and
a mechanical device for moving the configuration for applying pressure onto the measurement areas into a working position with respect to the planar support.

12. The device of claim 11, further comprising a template that is applied to the spread-out planar sanitary product to define the measurement areas.

13. The device of claim 12, wherein the configuration for applying pressure onto the measurement areas extends through the template.

14. The device of claim 11, wherein the configuration for applying pressure onto the measurement areas is designed to load each measurement area with an individual, predetermined pressure.

15. The device of claim 11, wherein the mechanical device is designed like a portal.

16. The device of claim 11, wherein a flatly extending plate-shaped and liquid-absorbing porous transfer element is applied at least over part of the planar extension of the spread-out sanitary product and the element for determining moisture is designed for measurement on the flatly extending plate-shaped transfer element.

17. The device of claim 16, further comprising a device for pressing the spread-out planar sanitary product and the flatly extending plate-shaped and liquid-absorbing porous transfer element, disposed on the sanitary product, against each other.

18. The device of claim 17, wherein the device for pressing the spread-out planar sanitary product and the transfer element disposed thereon comprises an element for exerting a pressure for loading the sanitary product from a side opposite to the transfer element.

19. A device for performing a method, the method for determining a moisture content of an absorbent sanitary product, a diaper, an incontinence pad, incontinence briefs or a sanitary towel, the method comprising the steps of:
a) applying liquid to the sanitary product under predetermined conditions;
b) spreading out, following step a), the sanitary product in a flat manner;
c) defining a plurality of zoned measurement areas over a planar extension of a spread-out sanitary product; and
d) taking one measured value for each measurement area or with respect to each measurement area;

the device comprising:
an element for determining the moisture in a respective measurement area to be considered or with respect to a respective measurement area to be considered, wherein said element for determining the moisture comprises a configuration for applying pressure onto the measurement areas in correspondence with a configuration of zoned measurement areas; wherein the configuration for applying pressure onto the measurement areas has a plurality of dies that are individually controlled and/or moved independently of each other and are applied against the measurement areas.

* * * * *